United States Patent [19]
Ridgeway et al.

[11] Patent Number: 5,879,628
[45] Date of Patent: Mar. 9, 1999

[54] BLOOD COAGULATION SYSTEM HAVING A BAR CODE READER AND A DETECTING MEANS FOR DETECTING THE PRESENCE OF REAGENTS IN THE CUVETTE

[75] Inventors: Helen J. Ridgeway; Eldon J. Pavelka, Jr., both of Beaumont; Edward L. Galloway, Lumberton; Frank A. Fertitta, Jr., Vidor; Bruce R. Petty, Beaumont, all of Tex.

[73] Assignee: Helena Laboratories Corporation, Beaumont, Tex.

[21] Appl. No.: 847,225

[22] Filed: May 1, 1997

Related U.S. Application Data

[60] Provisional application No. 60/016,952 May 6, 1996.
[51] Int. Cl.[6] .............................. G01N 33/00; B01L 3/02; G06K 7/10
[52] U.S. Cl. .............................. 422/73; 422/100; 235/462
[58] Field of Search ..................................... 235/462, 454; 422/100, 73, 63, 64, 65, 66, 67; 436/54

[56] References Cited

U.S. PATENT DOCUMENTS

| | | | |
|---|---|---|---|
| 3,656,473 | 4/1972 | Sodickson et al. | 235/487 |
| 4,369,361 | 1/1983 | Swartz et al. | 235/470 |
| 4,935,875 | 6/1990 | Shah et al. | 235/462 |
| 5,286,959 | 2/1994 | Demachi | 235/462 |
| 5,358,691 | 10/1994 | Clark et al. | 422/64 |
| 5,359,184 | 10/1994 | Froehlich et al. | 235/454 |
| 5,551,941 | 9/1996 | Howell | 422/72 |
| 5,595,664 | 1/1997 | Stanford et al. | 422/65 |
| 5,637,854 | 6/1997 | Thomas | 235/462 |

*Primary Examiner*—David P. Porta
*Assistant Examiner*—Diane I. Lee
*Attorney, Agent, or Firm*—Dorsey & Whitney LLP

[57] ABSTRACT

A method and apparatus for handling samples such as blood samples for hemostasis. The sample is transferred from a test tube into a cuvette which has been released from a supply of cuvettes. Prior to transferring the sample, a needle is introduced into the sample and automatically senses the level or height of the sample in the test tube. The presence of vials of reagent is optically confirmed. Reagents are to be delivered through a delivery tube into the cuvette and the delivery tubes are initially primed with reagent. The presence and orientation of the cuvette are verified and the sample transferred into the cuvette, the reagent automatically delivered into the cuvette, and the reaction such as, but not limited to, blot clotting occurs in the cuvette. The occurrence of the reaction is optically confirmed. The system and method controls the sequential release of stacked cuvettes in addition to confirming the presence and proper orientation of the cuvettes.

25 Claims, 15 Drawing Sheets

BLOOD COAGULATION SYSTEM HAVING A BAR CODE READER AND A DETECTING MEANS FOR DETECTING THE PRESENCE OF REAGENTS IN THE CUVETTE

CROSS-REFERENCE TO RELATED APPLICATION

The present application is based upon provisional application 60/016,952 filed May 6, 1996 which is hereby incorporated by reference. The documents identified as Appendices 1 through 8 in the provisional application are hereby incorporated herein by reference.

BACKGROUND OF THE INVENTION

The invention is a hemostasis analyzer system used for measuring clotting times on samples of human plasma. Analyses for Prothrombin Time (PT), Activated Partial Thromboplastin Time (aPTT), Thrombin Clotting Time (TCT), Fibrinogen and Factor Assays (Factors II, V, VII, VIII, IX, X, XI and XII) may be performed using this invention. Additional tests may be performed if data is provided as an input to the system. The invention is intended for in-vitro diagnostic use.

The invention automates or eliminates many of the steps of conventional hemostasis procedures which depend for their reliability on the technique and skill of the laboratory technician using the equipment. The present system automatically prepares dilutions and mixtures from samples and reagents, transferring them to cuvettes. Timed additions of reagent, incubation periods, and optical density measurements are performed automatically. Results are automatically quantitated, displayed and printed. As an option, the system will read bar coded information from sample tubes or vials. In addition, the invention may be interfaced with an LIS (Laboratory Information System) which will provide patient data and tests required, avoiding manual entry of that data.

SUMMARY OF INVENTION

In the preferred embodiment, up to 100 cuvettes can be used in a single batch of runs. Five reagent pumps deliver chilled reagents such as for PT, aPTT, TCT (Thrombin Clotting Time), Fibrinogen, and Factor Assays (Factors II, V, VII, VIII, IX, X, XI and XII).

The invention has three primary parts shown in the block diagram of FIG. 1, a computer, a sample handler and an optics handler. The computer generally identified as the CPU controls the operation of the entire system. The sample handler performs the automated functions necessary to prepare the raw samples for testing. The optics handler controls the processing of the samples with reagents and optically obtains the results.

A typical use of this machine would be by a technician in a hospital or clinical laboratory. The technician turns the analyzer system on and the system self-initiates which is a self-diagnosis on the software and hardware. If the bar code feature is utilized the reagents will be provided with bar codes. Hence, the bar code reader will scan the bar codes on the reagents to determine which reagents are present. The technician places cuvettes in a carousel. The system will initialize other features such as a liquid detection system and reagent heating which will be described in greater detail. Once all the initiation steps have been completed, with the reagents at the appropriate temperatures, the system is ready to process test tubes containing fluid samples.

A series of sample test tubes each with a stopper at the top and bar codes on the side, are loaded into test tube racks. The system attempts to read the bar codes from the test tubes. However, while a bar code reader is preferred, manual data input is within the scope of this invention. Thus the laboratory technician can provide manual input to the system to identify the patient or source of the fluid being tested. The system determines whether or not a test tube is present in the test tube rack and will move the test tube racks in the X direction as necessary to access the test tubes. The system ensures that the reagent vials contain proper reagents for the desired test and that they are of the appropriate temperature. Following these system checks, the system automatically primes the pump assembly. Next, the liquid detection system obtains samples from the test tubes, with the samples being withdrawn via a needle. The cuvette carousel will expel one cuvette and confirm that the cuvette is properly oriented. This cuvette is then placed in position to receive fluids from the needle. The needle obtains and deposits the appropriate amount of sample, and buffer, and factor solutions into the cuvette. Following this process, the cuvette slides down a chute and enters the optics handler.

The optics handler receives the cuvette on a transport belt in the optics assembly. The temperature of the liquid in the cuvette will now be raised to the appropriate temperature which in the preferred embodiment is 37° C. To obtain this temperature, heaters in the lid and the lower portion of the optics assembly are generally used. In the optics assembly, optic channels or "photoeyes" are used to detect the presence or absence and orientation of the cuvette. Appropriate reagents from the reagent assembly system are pumped by the pump assembly system to the cuvettes at the appropriate time. After the cuvettes have received the reagent, the optics detects when reactions (coagulation) occur in the cuvettes. These reactions are timed. Upon completion of the test, the cuvette is dumped into a waste container. Many variations are possible to the general steps described above in processing tests using an automated system.

DETAILED DESCRIPTION OF THE PREFERRED EMBODIMENT

Figure 1:
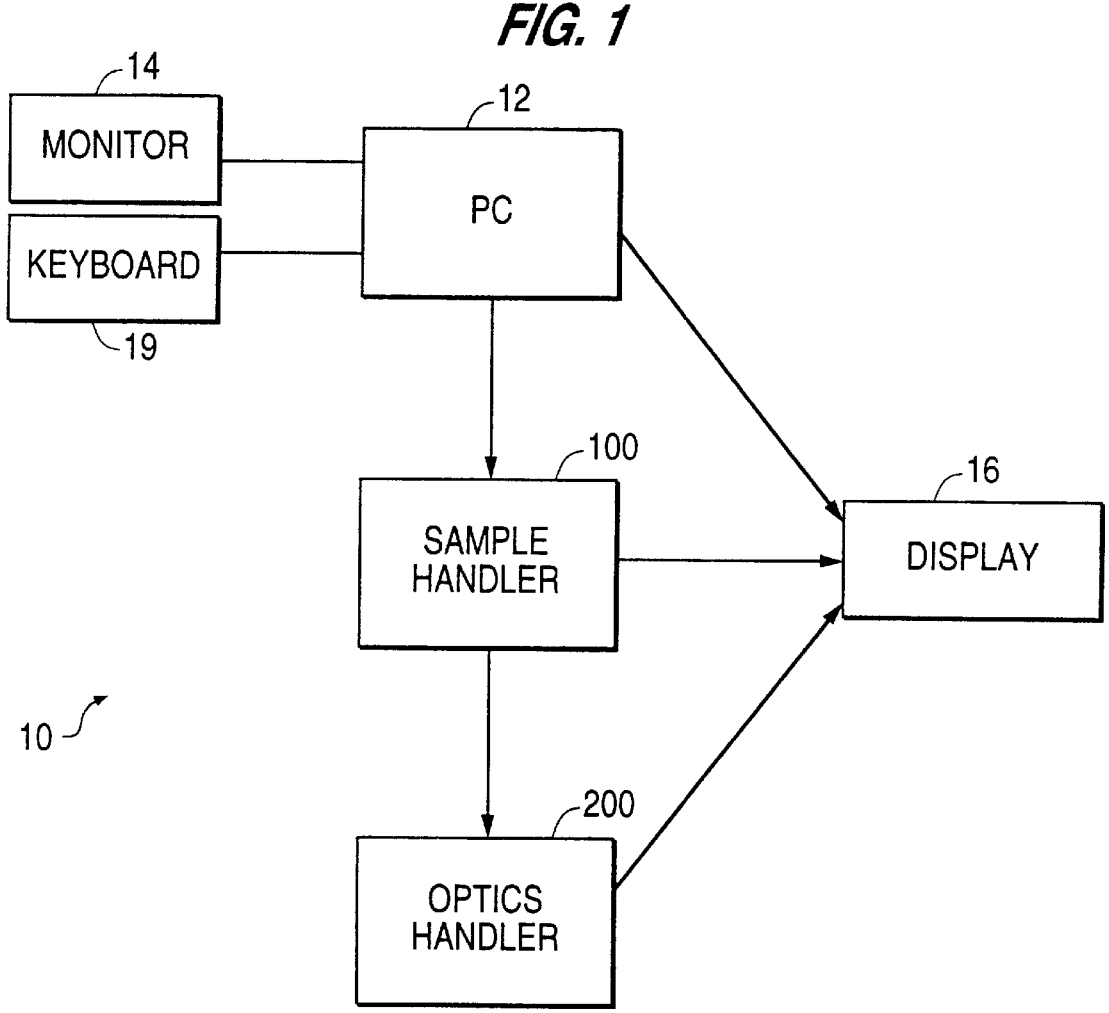
FIG. 1 is a diagram of the primary components of the automated hemostasis analyzer.

Referring first to FIG. 1, the system 10 in basic form includes a computer (sometimes identified as a CPU) 12 including a monitor 14, a primary display device 16, a keyboard 19, a sample handler 100 and an optics handler 200. Details of the sample handler and optics handler are provided with reference to other Figures. The appearance of the system 10 is illustrated in greater detail in FIG. 2, including the touch screen display 16, a printer 17, a disk drive, system power switch 20, secondary display 22, and a carousel 110. Various functional units of the analyzer are shown in block diagrammatic form in FIG. 3 including an 8-channel optical controller 24, a 4-channel temperature controller 26, a sample handler (controlling sample delivery and transport), three independent motor control modules 28, and the computer 12 for user interface and data storage. The temperature controller 26 includes a display 22, an incubator heater 32, an optics heater 34, a factor cooler 36 and a reagent cooler 38. "Y" and "Z" position encoders 40, 42 and a fluid sensor 44 are used by the sample handler to maneuver, pick-up exact sample amounts, transport, and deposit samples using a needle 118. A diluter 46 performs the dilutions required by each type of test. Many of these functions and steps per se are standard and will not be explained in greater detail.

Figure 2:
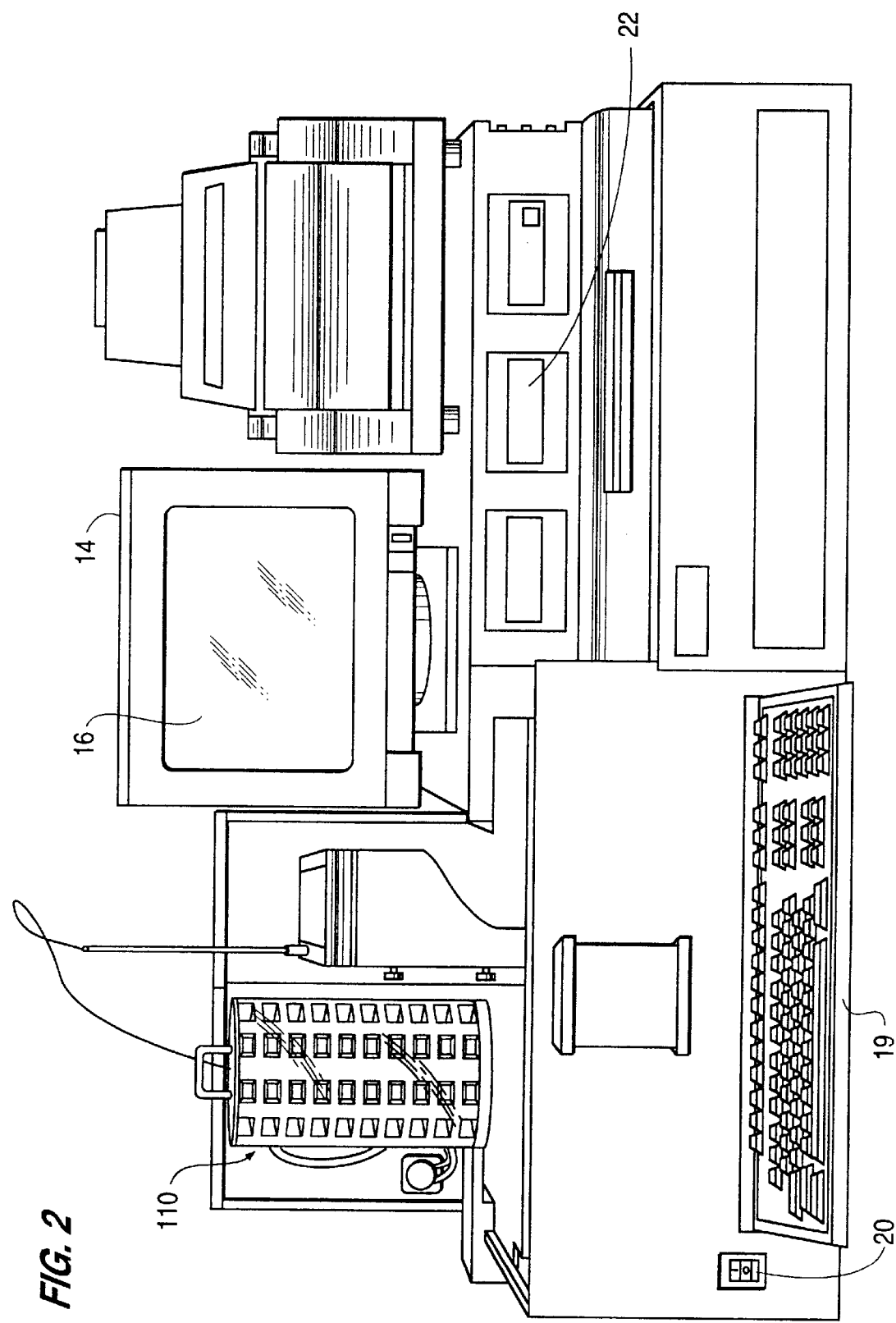
FIG. 2 is an illustration of the physical arrangement of the components of the system.

Most manual user input is through the touch screen 16 and keyboard 19 of FIG. 2. The user may select the type of test, start or stop the automatic sequence of operations, run standards, prime or purge the pumps, select instrument parameters, and change displayed menus. Patient data, control values, and other data are typically entered by keyboard 19, bar code reader 50, or the LIS interface. The printer 17 can be used automatically or on demand to print these results, profiles, standard curves or quality control records. RS232 outputs are provided for data transfer to external computers or a LIS (Laboratory Information System). When power is turned on for the apparatus (power switch 20) the system runs a 'self-test' to detect error conditions or potential problems. If an error is detected at any time, the computer responds by displaying an error message on the monitor 14.

Figure 4:
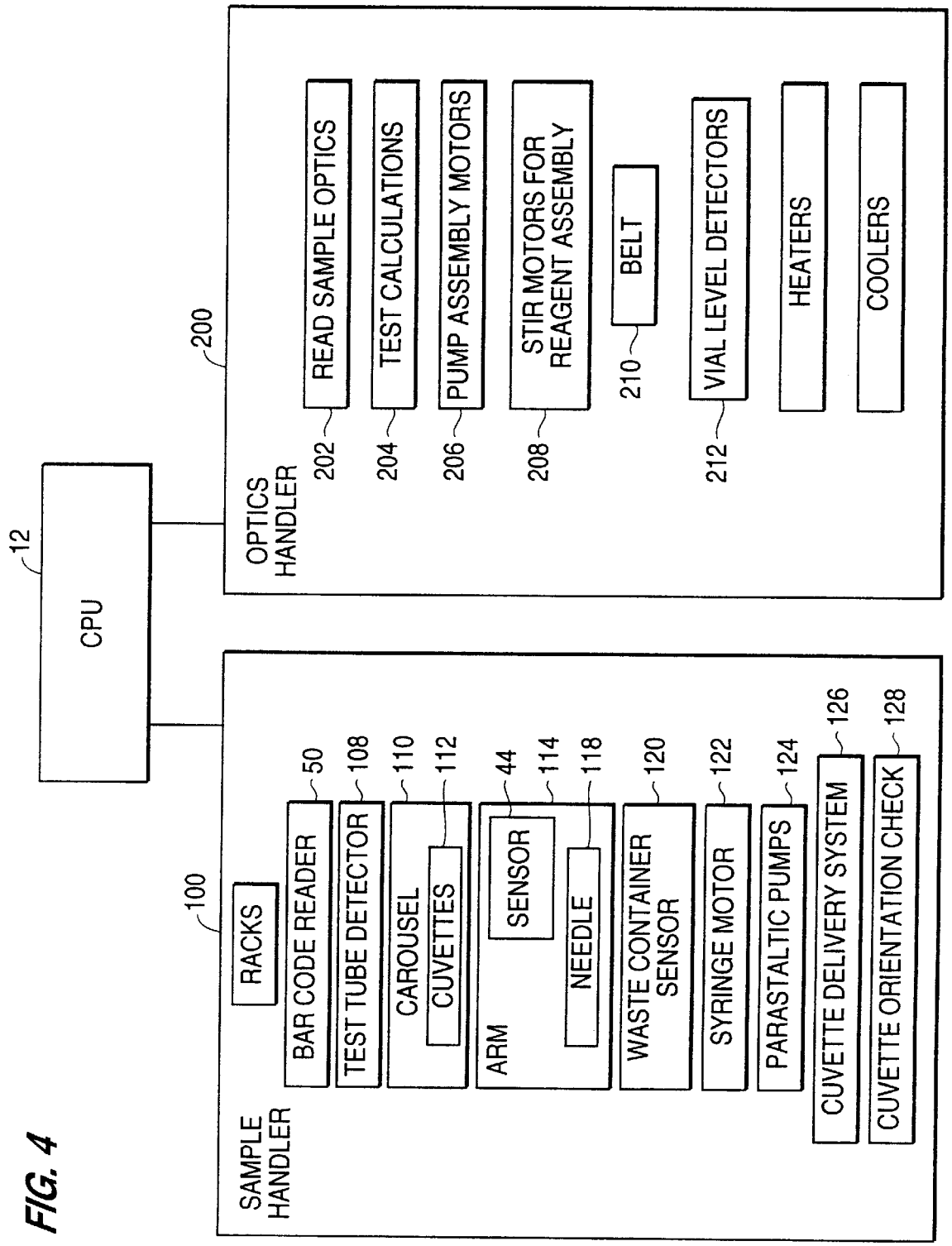
FIG. 4 is a block diagram of the sample handler and the optics handler.

FIG. 4 is a block diagram providing an overview of the functions and features of the three primary components of the preferred embodiment of the invention which are the computer/CPU 12, the sample handler system 100 and the optics handler system 200. The sample handler system 100 contains racks 102, 104, the bar code reader 50 referred to previously, a test tube detector 108, a cuvette carousel 110 with vertical racks of cuvettes, an arm 114 with a related fluid sensor 44 and a needle 118, a waste container sensor system 120, syringe motor 122, peristaltic pumps 124, cuvette delivery system 126 and a cuvette orientation verification system 128.

Figure 3:
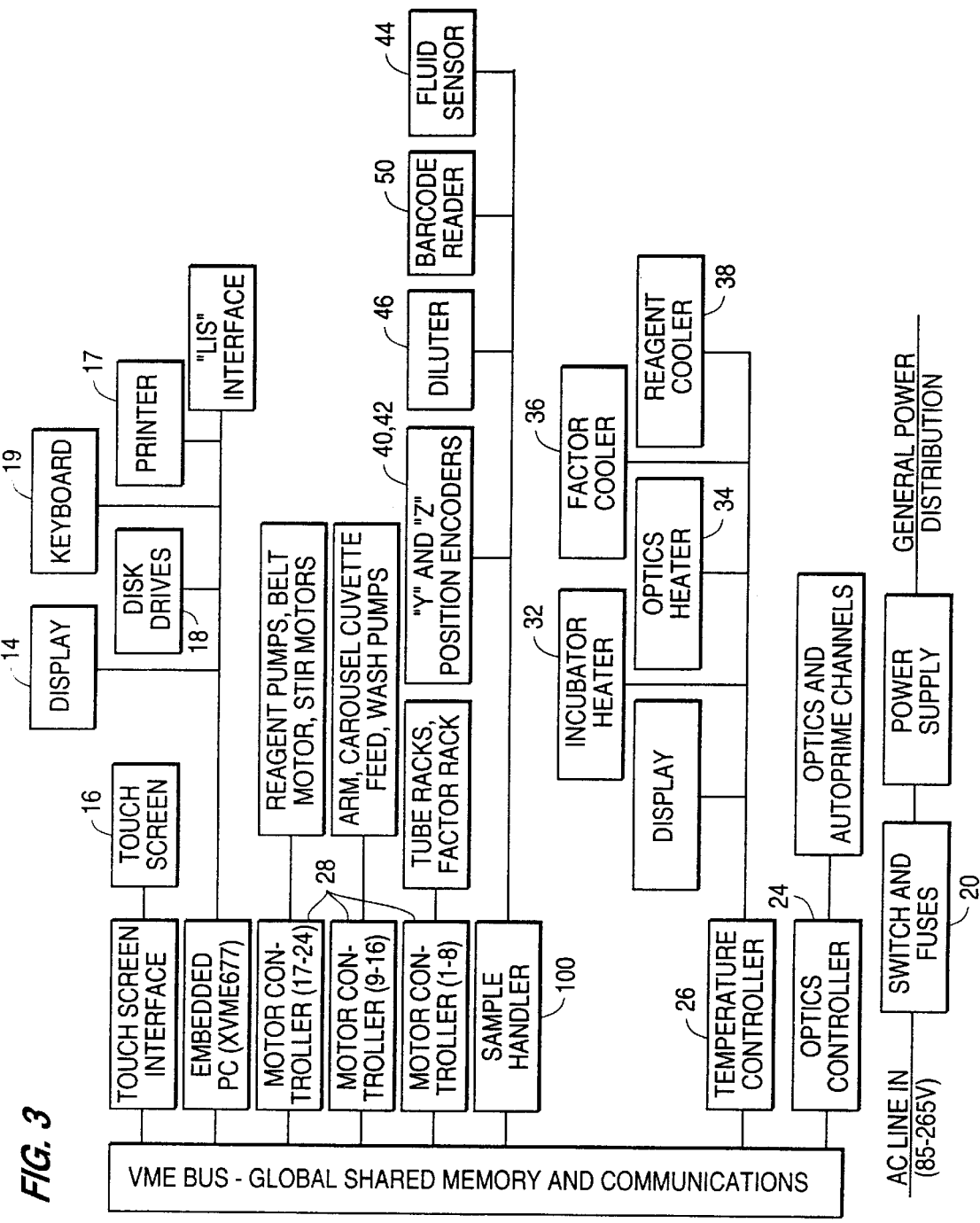
FIG. 3 is a detailed schematic of the processor.
Figure 5:
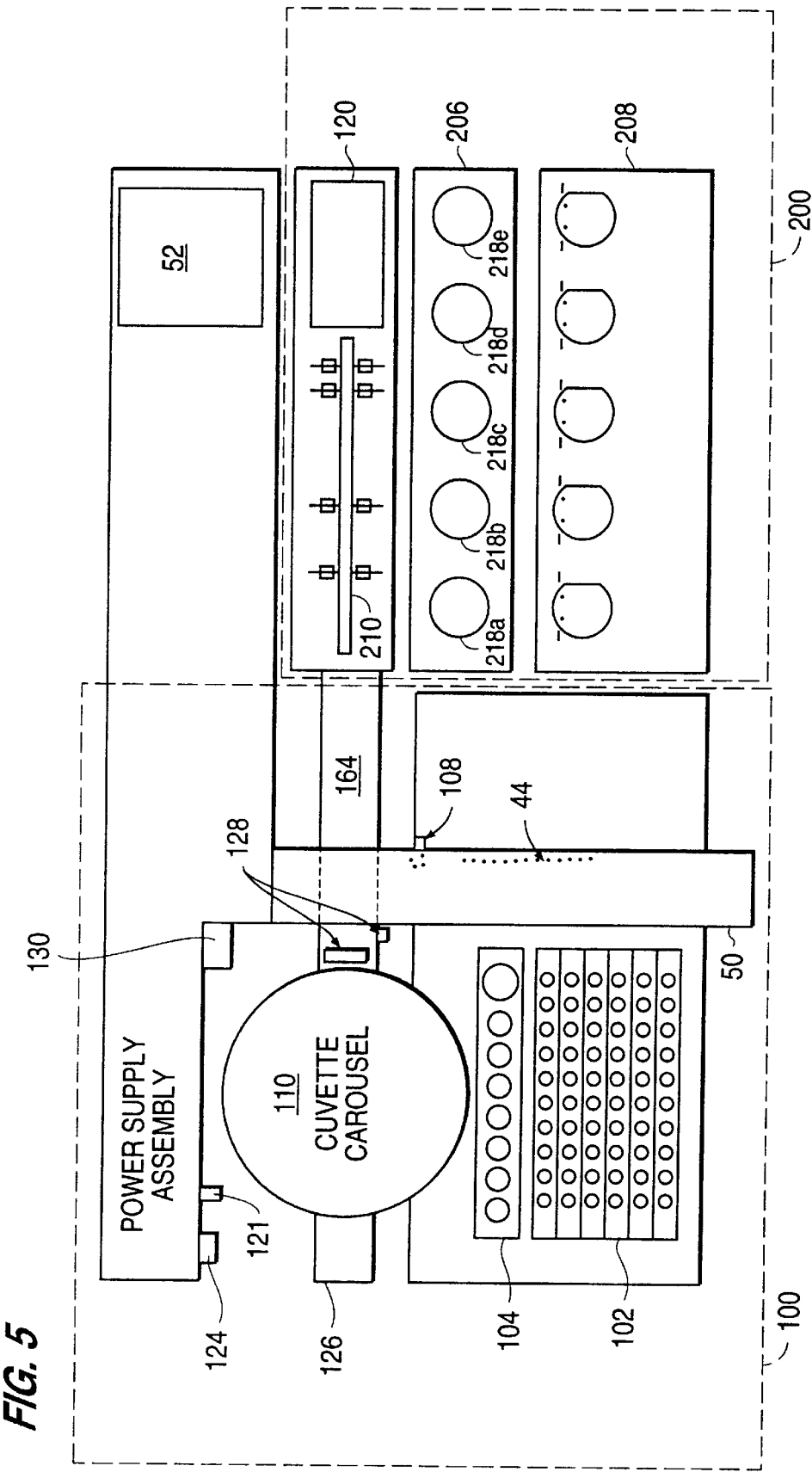
FIG. 5 is a detailed schematic of the sampler handler and the optics handler.

Referring next to FIG. 5 the processor or computer 12 which operates the system is preferably comprised of cards located within the card cage 52. The preferred cards within the card cage include a touch screen interface, b) embedded PC, c) motor controller (1–8), d) motor controller (9–16), e) motor controller (17–24), f) sample handler, g) temperature controller, and h) optics controller as shown in FIG. 3. The card cage contains the other circuits for operating the apparatus of the present invention.

The sample handler controls motion in the Y and Z coordinate planes. The sample handler will move the test tube racks 102 and the factor racks 104 in the X direction to position test tubes beneath the arm assembly 114 and in particular, the needle 118 of the arm assembly. The arm assembly moves the needle in the Y and Z planes. Alternate configurations moving the tubes or needle in X, Y and Z direction are possible. The movements are performed with stepper motors and encoders may be used for more accurate positioning. In the preferred embodiment, encoders 40, 42 are used for the Y and Z coordinate positions of the needle in the arm assembly.

The sample handler includes peristaltic pumps 124 and the syringe 121 with the accompanying syringe motor 122. Preferably there are two peristaltic pumps, one for flushing the inside of the needle through the syringe system and the second for pumping water to a wash basin 130 that is used to clean the outside of the needle. In the wash basin, the needle is cleaned with a continuous flow of cleaning solution.

The sampler handler includes the cuvette carousel 110, as previously mentioned, and the cuvette carousel holds vertical stacks of cuvettes. In the preferred embodiment, the cuvette carousel holds ten stacks of ten cuvettes each. The cuvette delivery assembly 126 includes those parts which allow the cuvette to be fed ultimately from the carousel to the chute and to the optics handler. The cuvette verification/orientation system 128 sense that the cuvette is in the proper position and orientation before the cuvette is permitted to receive samples and reagents.

The factor/buffer rack 104 holds the factors (chemical reagents) and buffers that are necessary in performing the various tests. The factors/buffers are maintained in bottles 105 in a position such that the needle, controlled by the arm assembly, may obtain the necessary quantities of factors or buffers. The test tube rack 102 holds the blood samples in test tubes 103.

The bar code reader 50 which is interfaced to the sample handler will input data from bar coded labels on the test tubes 103 when the instrument is in the bar code reading mode. The test tube detector system confirms the presence or absence of light from the bar code to determine whether a test tube 103 is present. The fluid sensor 44, together with the arm assembly and needle, sense fluid and assist in obtaining or withdrawing the proper amount of fluid from a test tube 103 in the tube rack 104, or from a factor bottle or buffer bottle in the factor/buffer rack 104.

Preferably, touch screen controls are used with the system monitor. Thus, with a touch of the finger on a box displayed on a screen 16, the user will change menus, make choices, and perform actions with the system. In addition, it is preferred that a keyboard 19 be used in conjunction with the touch screen. Alternatively, the keyboard may be used alone instead of the touch screen.

It is preferred that a small display 22 on the system be used in addition to the monitor display. An LED or LCD display is preferred. The small display in the preferred embodiment is shown in FIG. 2. The display indicates the processes which are in progress and the temperatures of different areas in the system. The monitor 14 provides displays of the system test parameters, test results, quality control data and other information. Menus on the monitor display are provided to guide the user through instrument operations. From any menu, the user may make selections by touching the screen 16 over the appropriate box. The user can also make a selection by using a "hot" key on the keyboard. If a word is boxed on the screen, the user may also press the first letter on the keyboard to select that function.

Figure 6:
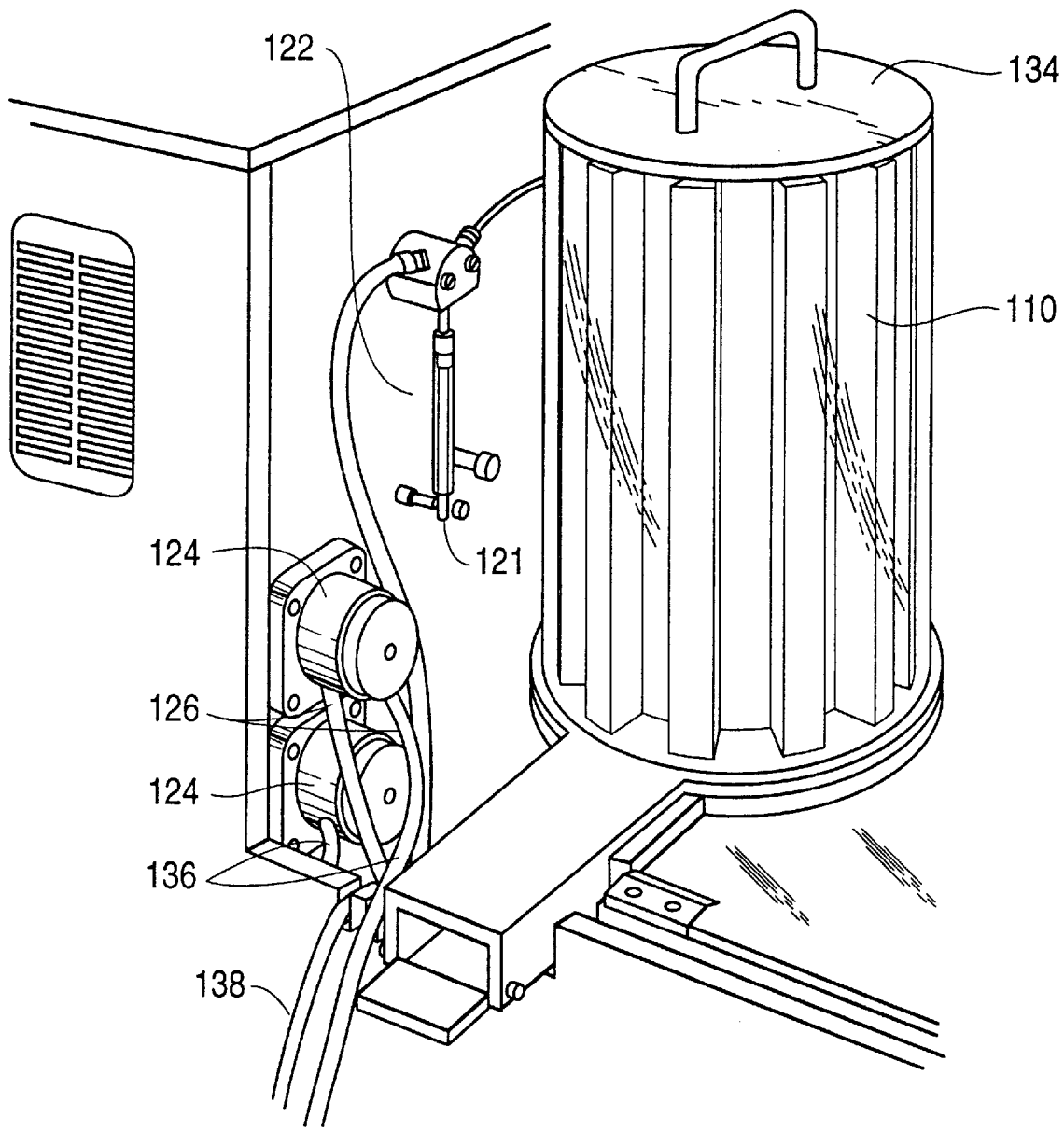
FIG. 6 illustrates part of the sampler handler, showing the cuvette carousel, the syringe system, and the pumps.

FIG. 6 is an illustration of part of the sample handler for one embodiment of the invention. In FIG. 6, a syringe 121 and a syringe motor 122 are shown for handling the exact quantities of fluid that the needle will withdraw from the test tubes or factor or buffer solutions in the factor/buffer racks. The syringe and syringe motor system is extremely precise and is connected to the needle through plastic piping. The cuvette carousel 110, which is covered by a cuvette carousel lid 134, holds vertical racks of cuvettes. The cuvette carousel is circular and is loaded with empty cuvettes from one side and the cuvettes are discharged from the opposite side for use by the system.

Two peristaltic pumps 124 are shown in FIG. 6 with fittings and delivery tubes 136. One peristaltic pump is for flushing the inside of the needle through the syringe and syringe motor system. The second peristaltic pump is for use in the wash basin 130 which washes the outside of the needle. Waste tubes 138 are shown leading away from the sample handler. The wash basin forces a solution up against gravity and the needle is lowered into the running solution.

Figure 7:
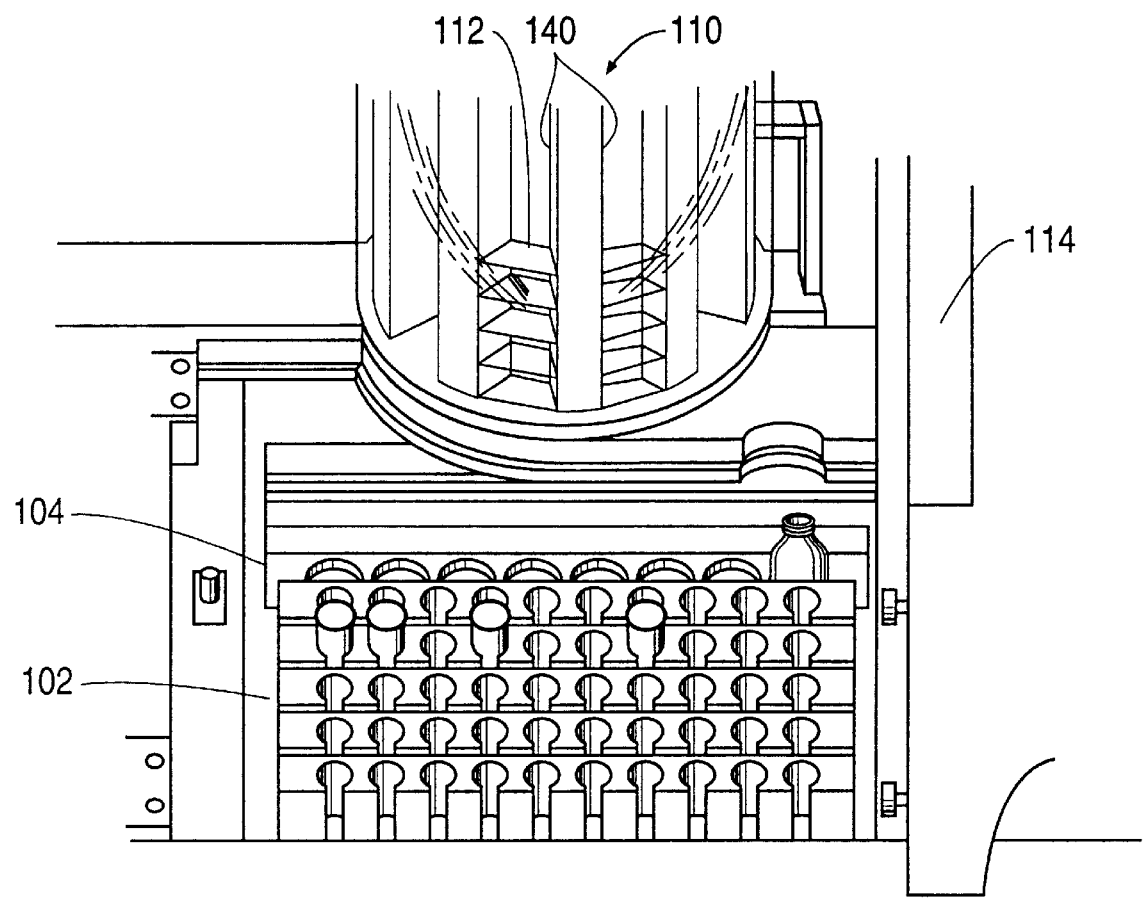
FIG. 7 illustrates a part of the sampler handler, showing the test tube racks and the factor/buffer rack.

FIG. 7 is a top view of the sample handler illustrating the test tube racks 102 and the factor/buffer rack 104. The sample handler arm 114 moves both the arm and needle in the Y and Z coordinate planes. The carousel includes the series of vertical racks or channels 140 and two partially-full racks, with cuvettes 112, are shown in FIG. 7.

Figure 8:
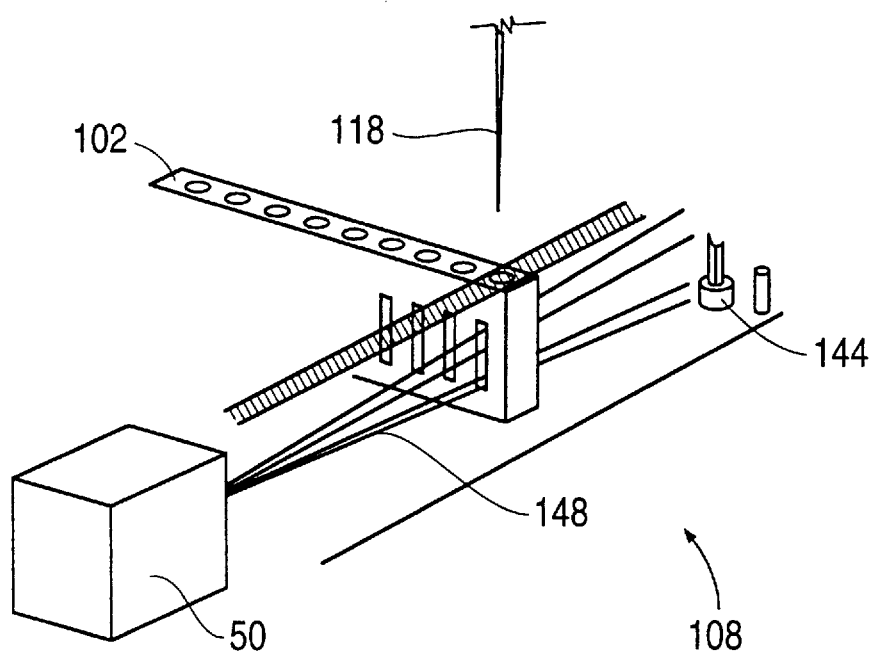
FIG. 8 is a diagram of the test tube detection system.

Referring to FIG. 8, the test tube detector system 108 for determining the presence or absence of a test tube 103 is explained in greater detail. An off the shelf bar code reader 50 reads bar codes on the factors/buffers bottles 105 and on patient test tubes 103. The reader preferably has its "depth of field" increased. In the preferred embodiment, the LED or laser light source from the bar code reader is further used by the system to determine the presence or absence of a test tube. Thus the test tube detection system 108 includes a photodetector 144, and software. With no obstructions between the light source and a photodetector, the light beam 148 from the bar code reader is received and a voltage threshold is set in the photodetector. This is referred to as initializing the bar code reader. During system operation, a test tube rack moves in position for a bar code on a test tube to be read. If a bar code cannot be read and the photodetector receives the same amount of light as when initialized, then a tube is "not" present. However, if, the photodetector receives a lesser amount of light, then a test tube is present, and the operating system can either read the bar code on the test tube to automatically commence tests, or alternatively indicate that a bar code was not present on the test tube. In the latter situation, the laboratory technician can override the system if a test tube without a bar code has been deliberately placed in the test tube rack. The following is a step-by-step description of the technique for determining the presence or absence of a test tube in the working location and, from these steps, those of ordinary skill can prepare and/or modify software as desired.

1) Test tube rack 102 moves into position (see FIG. 8).

2) Bar code reader 50 triggers and illuminates a beam 148 toward the photodetector 144;

3) Three possible conditions exist at this time:

a) no test tube—if the bar code scanner does not receive any signal reflected back from the test tube but the photodetector receives a signal above the threshold level;

b) test tube present with no bar code—if the bar code scanner does not receive any signal reflected back from the test tube and the photodetector receives a signal at the threshold level;

c) test tube present with bar code—the bar code scanner receives a signal reflected back from the test tube and the photodetector does not receive a signal.

4) After one of the three possible conditions have been determined, the system checks for any manual input (e.g., via the keyboard) and, if there are any discrepancies, an error condition will be presented. Otherwise, the system will proceed with sampling and testing.

Figure 9A:
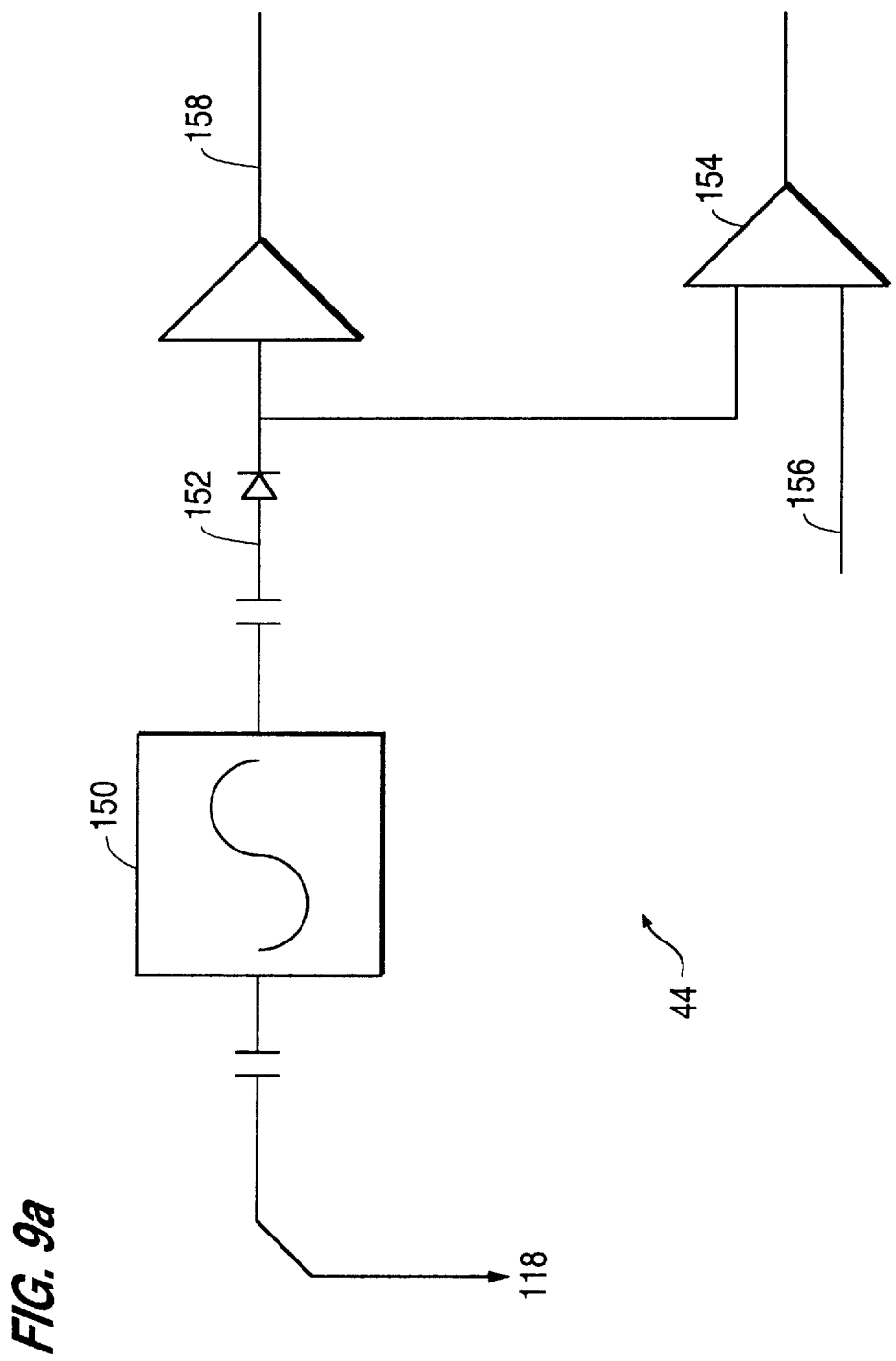
FIG. 9a is a schematic of the RF fluid level sensing circuit.
Figure 9B:
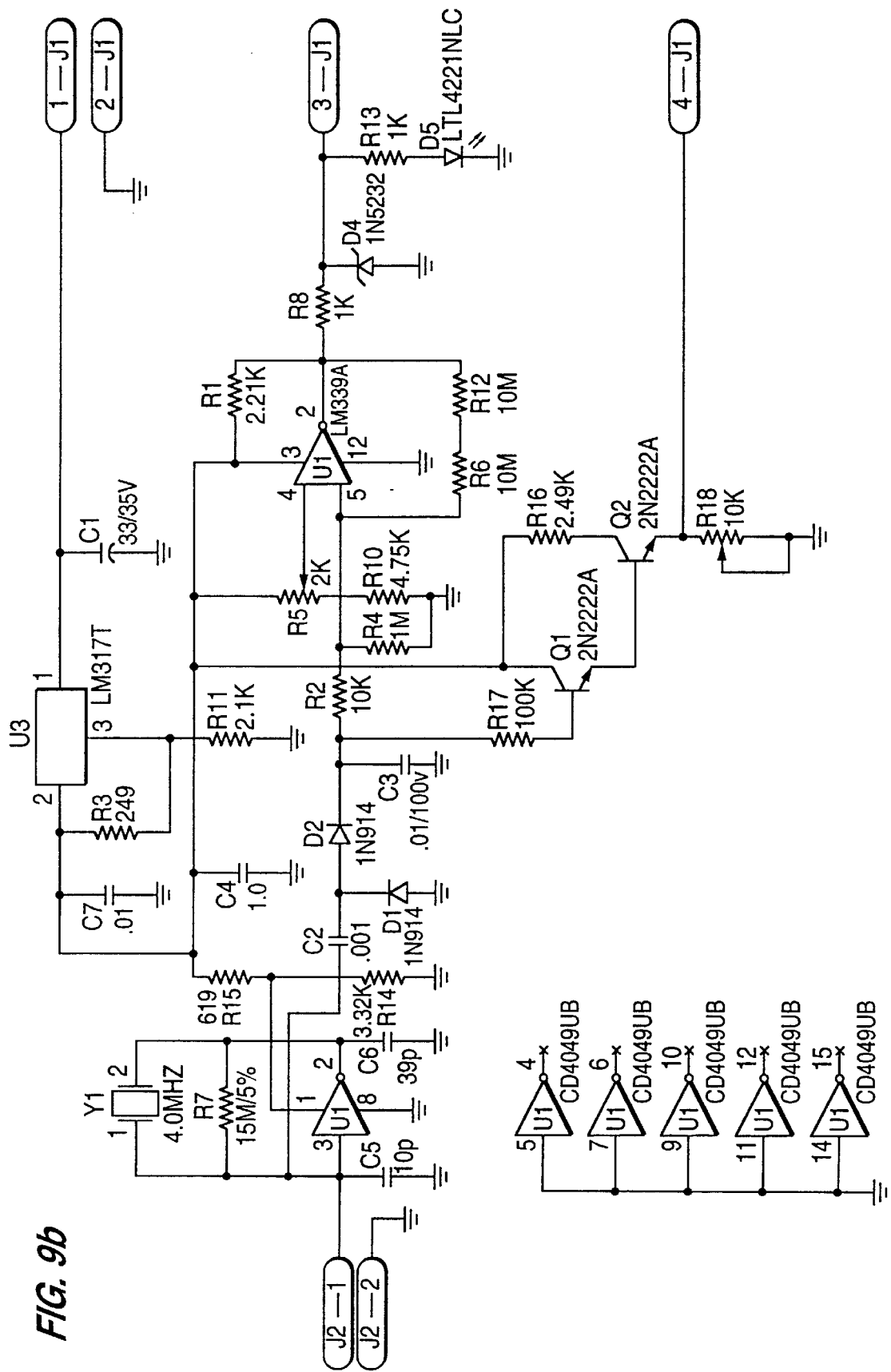
FIG. 9b is a detailed schematic of the RF fluid level sensing circuit.

Referring to FIGS. 9a and 9b, the preferred fluid sensor or level detector system 44 operates in conjunction with the arm 114 and needle 118. The fluid level detector operates in the RF range and only the needle makes contact with the fluid. Thus the needle 118 pierces the rubber stopper on the tube and then functions as the sensor. The preferred fluid detector is based on a radio frequency CMOS oscillator 150 similar to the clock oscillators found in most personal computers having an output frequency optimally at 4 mhz. This frequency is sensitive to fluid and lacks sensitivity to surrounding metal used to build the instrument in which the fluid level detector is utilized. Variations from this frequency are possible. The oscillator output is coupled to the sample needle via a 50 ohm shielded cable. The shield extends to the sample needle thus reducing radiated RF energy to a few microwatts because of the needle length which is extremely short. The oscillator output is capacitively coupled 152 to a rectifier, filtered, and then fed into a comparator 154.

The theory on which the detector functions is that when the needle contacts the fluid and is capacitively coupled to ground, the sine wave oscillator voltage output drops. In operation, as the needle comes into contact with fluid in a sample tube, the oscillator output is "pulled" down thereby reducing the DC voltage the comparator 154 is sampling, causing it to compare. The comparator reference voltage 156 is set via a resistor divider and the comparator compare point is set according to the depth desired in the sample tube. The less sensitive the comparator is set, the deeper into the sample the needle must travel for the "pull" on the oscillator to cause a compare condition.

A buffered analog output voltage 158 is derived from the rectified oscillator voltage which is fed into an analog to digital converter. This allows the raw data from the level sensor to be interpreted by software to greatly increase the dynamic range of the sensor. The circuit shown in FIGS. 9a and 9b, include both a digital and analog output. Both outputs are not necessary to accomplish the goal of sensing the presence/level of fluid. Either an analog or digital output may be arranged to perform this function. However, it is preferred that an analog output be used along with an analog to digital converter and software to determine whether or not fluid is present. The software processes the analog voltage to obtain very sensitive readings which are not affected by metal objects. A brief description of the algorithm used to process the raw data follows:

The sensor is placed in an "unsensing" state by moving the needle to a clear location. The voltage is read to determine the upper limit. The sensor input is then shorted to ground at the needle to check the lowest voltage reading.

During normal operation, the sensor is read while the needle is in a dry location. A fixed voltage amount is subtracted from this reading to use as a threshold to know when the needle actually makes contact with a liquid. During the operation of the system, the needle will pierce the stopper on a test tube containing a patient sample. Following the piercing of the stopper, but prior to making contact with fluid, the detection system will take a reference voltage reading. Upon the system taking the reference reading, the needle will continue downward until a voltage drop, below the reference voltage, (which is greater than the threshold) is detected. This will be the "wet" sera. The system can then determine exactly how far to plunge the needle into the sample in order to get the required sample volume. The system accomplishes this objective by using a look-up table which will show what type of test tube or vial is being used for the current test. Since the look-up table indicates the capacity of the test tube or vial and where the top edge of the sample will be located, the system can determine how far down to place the needle in order to extract the correct amount of liquid.

During system set-up the detection system is initialized. Preferably, to initialize and test the system, the needle will use a bottle of buffer solution. Buffer solution is detected and then "picked-up" as a control in order to determine appropriate voltage drops for system initialization.

When in operation in the system, the needle will generally pick-up a certain volume of buffer solution first, take a new voltage reference reading, and then pickup blood. The voltage reference reading may be taken after the needle pierces a stopper in the sample test tube containing blood. Using this detection system, the sample handler is able to determine the appropriate location of the needle in the Z plane to perform various functions.

After the needle 118 penetrates the stopper and the fluid sensor system 44 confirms that the needle has reached the fluid in the test tube, the fluid is withdrawn through the needle to be deported into a cuvette.

Figure 10A:
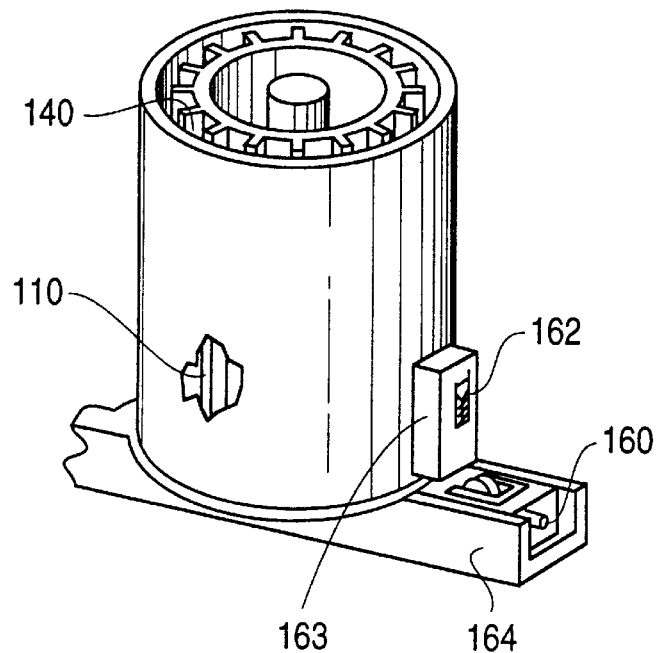
FIG. 10a is an illustration of the cuvette carousel.
Figure 10B:
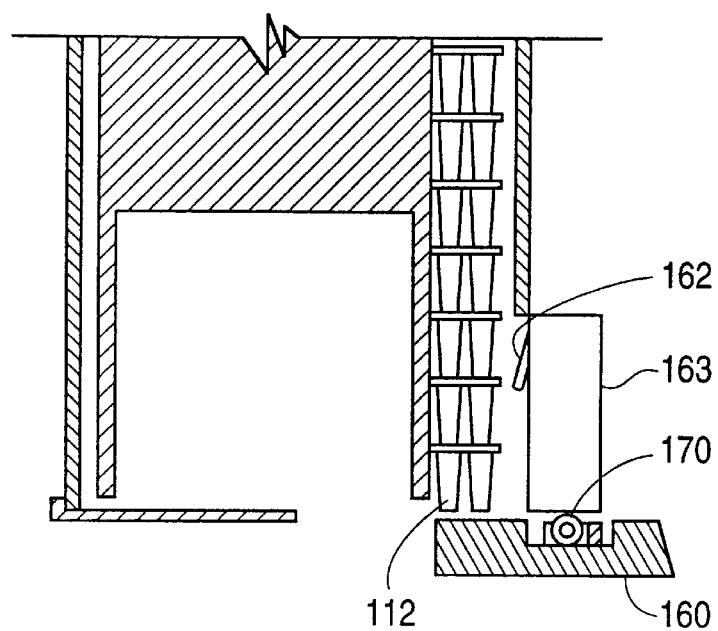
FIG. 10b is an illustration of a side-view of the cuvette carousel in the front loading position.
Figure 10C:
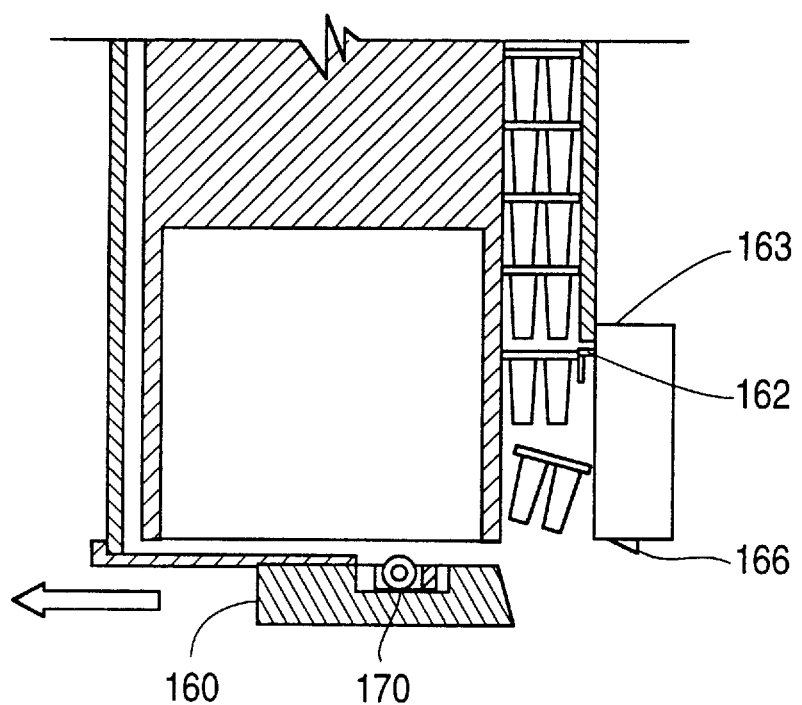
FIG. 10c is an illustration of the cuvette carousel in the back loading position.

Referring to FIGS. 10*a*, 10*b* and 10*c*, the cuvetted delivery system 126 for downloading a cuvette from a cuvette rack in the cuvette carousel ejects or releases a cuvette 112 from the carousel 110 or turret. A plunger 160 and compression spring 162 are positioned in a spring block housing 163 which is mounted to the outside of the carousel 110. The plunger and spring are used to release or eject a cuvette from a rack 140 in the cuvette carousel. The plunger moves laterally from a first position under a rack 140 in the carousel (FIG. 10*b*) to a second position inwardly of the rack (FIG. 10*c* ). There may be as many as ten cuvettes 112 vertically aligned and in vertical contact within a single rack 140. It is necessary to eliminate this vertical contact from the bottom cuvette in the rack so that only the bottom cuvette will be released. In this manner only a single cuvette will be released. In the position illustrated in FIG. 10*b*, the plunger 160 blocks the release of the cuvettes. The plunger includes a roller bearing 170 which contacts an actuator rod 166 in the spring block housing 163. In this position, the compression spring 162 in the housing is moved out of contact with the vertical column of cuvettes.

As the plunger is moved to the left as indicated by the arrow in FIG. 10*c*, the roller bearing 170 moves clear of the actuator rod 166. The compression spring 162 biases the actuator rod into the downward position (FIG. 10*c*) and, when the plunger is removed from under the actuator rod, the spring urges the rod downward and, at the same time, the spring moves toward the vertical rack of cuvettes to contact the cuvettes. Specifically, the spring contacts the second cuvette from the bottom and urges the second cuvette against the carousel rack. This holds the second cuvette, and all the cuvettes above the second cuvette, in the rack while relieving the pressure on the bottom cuvette. The bottom cuvette alone thus descends into a cuvette chute 164. Then the plunger moves forward (to the position in FIGS. 10*a* and 10*b*) and the roller bearing 170 urges the rod 166 upwardly against the compression spring 162 thus causing the compression spring to move out of contact with the vertical rack of cuvettes. The cuvettes then move downwardly under the force of gravity, so that the cuvette which was formerly the second from the bottom now moves into contact with the plunger and becomes the bottom cuvette.

The following is a step by step procedure describing the release of the cuvette for processing:

1) The carousel 110 moves a column or rack 140 of cuvettes 112 into position over the cuvette chute 164;

2) The plunger 160 retracts to the back loading position (see FIG. 10*c*) and the roller bearing 170 moves clear of the activator rod 166, thus deactivating the actuator rod;

3) With the rod 166 deactivated, the compression spring 162 applies pressure to the cuvettes in the column. This relieves the first cuvette of any pressure placed on it by the cuvettes in the column;

4) The plunger 160 retracts a sufficient distance to allow the cuvette to free fall into the cuvette chute 164;

6) When the plunger 160 returns to the forward position (see FIG. 10*b*), the roller bearing engages the actuator rod which retracts the compression spring (see FIG. 10*b*) and releases the pressure on the cuvettes in the column.

Figure 11A:
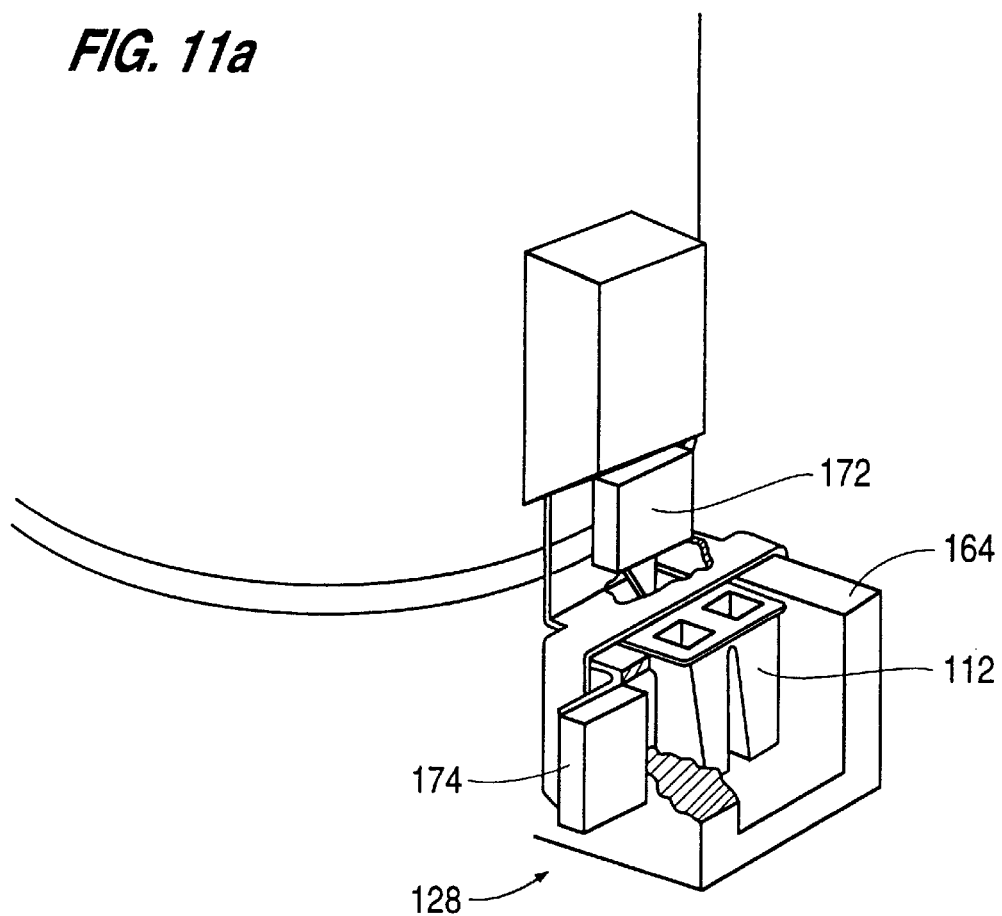
FIG. 11a is an illustration of the cuvette orientation/verification system.
Figure 11B:
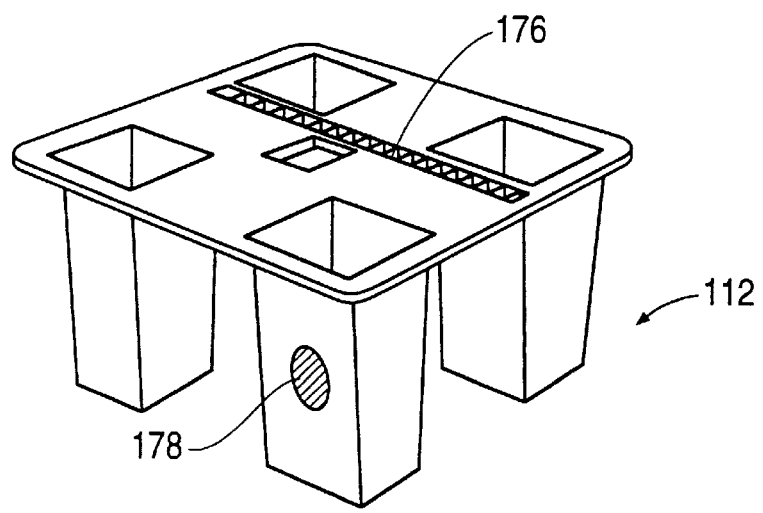
FIG. 11b is another illustration of the cuvette orientation/verification system.

Referring next to FIGS. 11*a* and 11*b*, positive cuvette orientation system 128 includes two photodetectors 172, 174 positioned at right angles to each other. Preferably one photodetector 172 is positioned above the chute 164 where the cuvettes are released from the carousel and the other photodetector 174 is positioned adjacent the chute. The individual cuvette 112 includes a first portion 176 on the flat top of the cuvette and a second portion 178 on a side wall of the cuvette. As the cuvette is discharged from the carousel, it is important to confirm that the cuvette has actually been released and that the cuvette is oriented properly to receive the sample and the reagents. As the cuvette 112 is released from the carousel 110 and moves into the chute 164, the cuvette moves beneath a first photodetector 172 which reflects a beam of light off the flat top portion 176 of the cuvette top surface. If the first photodetector does not receives the desired reflected signal, an error condition is generated. The error could indicate that the cuvette is absent or that the cuvette was inverted. As the cuvette continues to move along the chute, a transverse beam (across the direction of travel within the chute) is generated from the second photodetector. If this transverse beam is not reflected back from the side wall 178, then the second photodetector generates an error signal indicating misalignment of the cuvette. If both photodetectors receive positive signals, this is a confirmation that a cuvette is properly oriented. Any other condition generates an error signal to prevent any attempt at placing samples into the cuvette.

The optics handler 200 will now be described in greater detail. Referring to FIGS. 4 and 5, the optics handler includes a variety of sub-systems which perform various functions including reading sample optics 202 and calculating tests 204. The optics handler controls the pump assembly motors 206 for pumping reagents, the stir motors 208 for stirring the reagents, the transport belt 210, the vial level detectors 212, heaters and coolers 216. The optics handler 200 performs the clot analyzing functions of the invention. In the preferred embodiment, up to twenty samples (five cuvettes each containing four samples) can be placed on the transport belt 210 for automatic analysis. Five reagent pumps 218a, 218b, 218c, 218d and 218e in the optics handler deliver chilled reagents for PT, APTT, Thrombin Clotting Time, Fibrinogen, and Factor Assays (factors II, V, VII, VIII, IX, X, XI, and XII). Using five pumps reduces the need for a changeover when performing subsequent tests.

Operation of the optic handler components are controlled by the computer.

A delivery or transport belt 210 receives cuvettes from the chute 164 and moves the cuvettes along the optics assembly line. The delivery belt uses photodetectors to verify the proper positioning of the cuvettes along the belt as is conventional. While the cuvettes are moved along this belt, the cuvettes are being heated and it is preferred that the cuvettes and reagents reach a stable and optimum temperature of 37° C. before the tests are actually performed. The belt is moved along at the speed necessary for the desired test and thus the speed is controlled by the laboratory technician selecting the specific test. It is within the skill of the art to program the transport speed based upon the test selected, such information being easily stored in a look up table. Thus the belt speed changes depending on the test which has been selected, and the time that the cuvette travels along the belt will change depending upon the test and user inputs.

Referring to FIGS. 12, 13a, 13b, 14a, and 14b, a non-invasive level detector for determining the levels of reagent fluids in the reagent bottles uses the properties of light and occlusion to non-invasively monitor if fluid is available in a vat or bottle. The method works with both opaque and clear fluids. In the fluid or liquid level detection system 212, an optic block 226 is positioned adjacent a bottle or vat 105 of reagent. A LED transmitter 228 and photooptical coupler or photodetector 230 are used in conjunction with a collimator hole 232 bored or formed in the optic block. The light in the form of a narrow beam 234, such as from an LED or HeNE laser is directed through a chord of a clear polystyrene container or bottle 105. In plan view, the beam of light cannot travel through the diameter of the container but must be off-center, e.g., as a chord 235 of a circle in FIG. 13a. The photodetector 230 is placed at the opposite side of the bottle to receive the light beam. As fluid is placed into the bottle the beam deflects as at 236 due to the optical density of the fluid. The deflection (or diffraction) diverts the beam away from the photodetector, hence the photodetector will not receive the beam. This indicates that fluid is in the container or bottle 105. If the fluid is opaque, there is the added benefit of reduction of light through absorption loss. When the vat or bottle is removed, e.g., for replacement or replenishment, the photodetector receives the beam of light, i.e., the light beam is not deflected. Therefore, the preferred detection system indicates the absence of a bottle and the presence or absence of fluid if the bottle is present.

Figure 12:
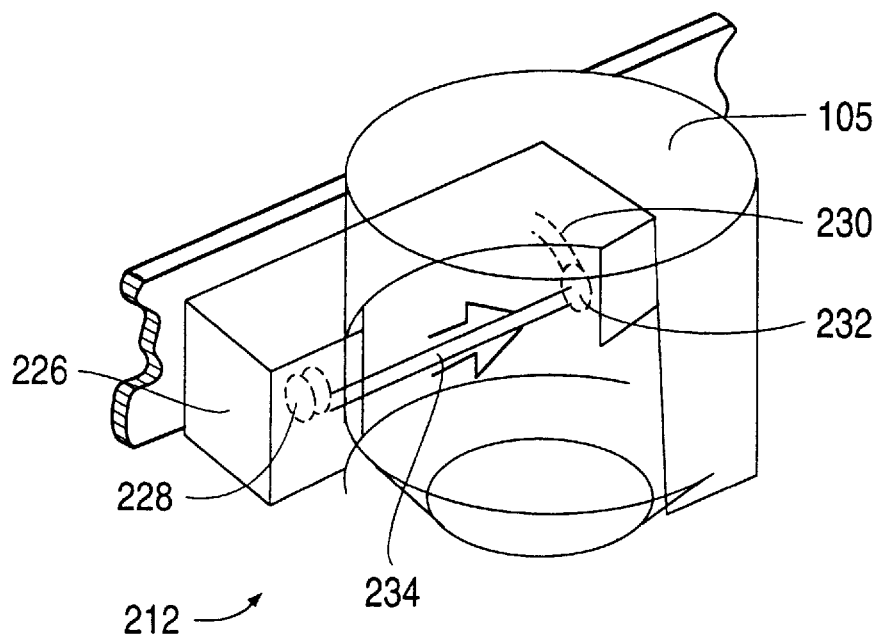
FIG. 12 is an illustration of the noninvasive method of reagent level detecting.
Figure 13A:
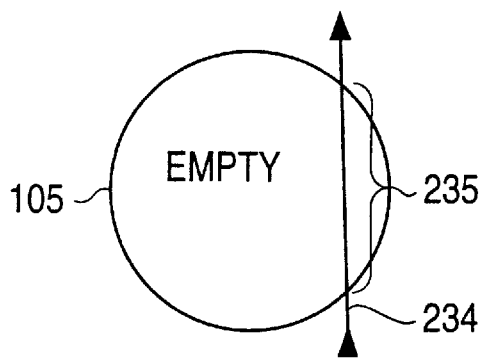
FIG. 13a is an illustration of a step in the reagent level detecting method.
Figure 13B:
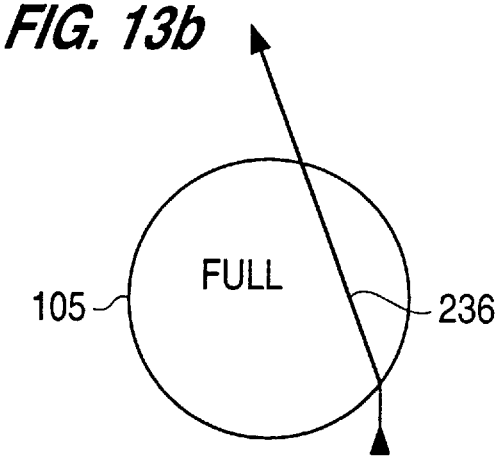
FIG. 13b is an illustration of a second step in the reagent level detecting method.
Figure 14A:
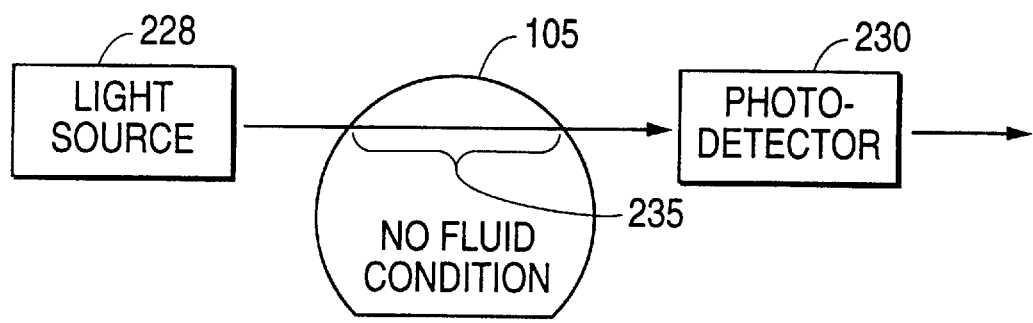
FIG. 14a is an illustration of the reagent level detection of the absence of fluid.
Figure 14B:
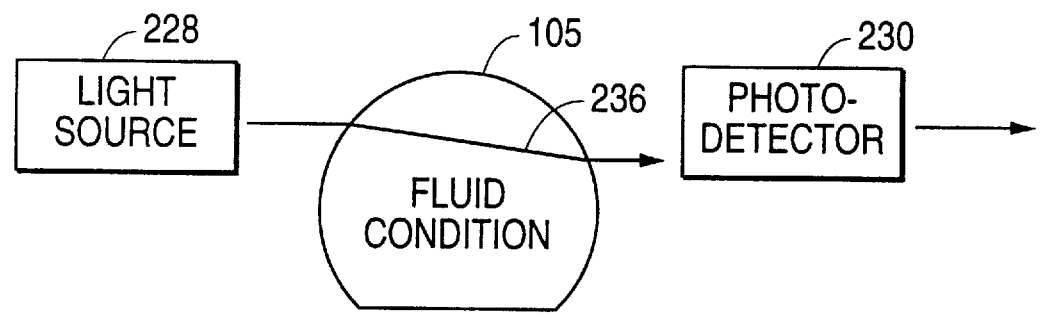
FIG. 14b is an illustration of the reagent level detection of the presence of fluid.

FIG. 12 illustrates the physical arrangement of the liquid level detection system; FIGS. 13a and 14a indicate the presence of a container 105 which is empty (or the absence of a container) and FIGS. 13b and 14b indicate the presence of fluid at the vertical level (height) of the detector. The height of the detector may be selected to insure sufficient fluid for the quantity of tests which can be performed without further intervention by the laboratory technician.

The pump assembly system 206 of the optics handler pumps fluids from the reagent vials or bottles 105 to the cuvettes. The volume of reagent transferred to the cuvettes is preferably an exact amount of reagent. In the preferred embodiment, the pump assembly system utilizes exact volume tubing to accomplish this function. The exact volume tubes are located at the pump assemblies. The exact volume tubes are plastic pipes which have been tested so that a certain length of the pipe holds exactly the volume of reagent that is needed for a particular test. Thereafter, once the pump assemblies are primed, the exact volume tubes are emptied each time a particular dose of the reagent is needed.

Autopriming is a process in the present invention in which the activating reagents are filled into their respective delivery tubes without assistance from an operator. This method is as follows. A standard cuvette 112 with four wells is discharged from the carousel and transported by the belt 210 until two of the wells are positioned under two delivery tubes of the specified reagent. At this area is a standard photodetection system used for timing the formation of a clot. The software/electronics combination initializes or "nulls" the light change caused by the empty cuvette in the optics path. A predetermined threshold is set by the software for detecting converted analog readings from the optics detector. This is referred to as a z-axis threshold value for the photodetection system, the z-axis referring to the vertical axis when the system is viewed from the front as is conventional. The associated pump 218 turns for a predetermined number of cycles, moving fluid into the first delivery tube. After a few revolutions any fluid (reagent) is now ejected into the cuvette. The photodetection system checks for the presence of fluid in the first cuvette well by measuring the change of light intensity at the threshold z-axis value. If there is no change in light intensity, then no liquid is detected and an error message is displayed. If, however, the desired reduction in light intensity was noted by the photodetector, this confirms that first reagent was pumped into the first well. Thus the first reagent pump has been primed so that the desired amount of reagent (using the exact volume delivery tube) will be pumped into a subsequent cuvette when an actual sample is being tested. Then the system is repeated for the second reagent, third reagent, etc. This procedure provides for the priming of each pump. The reagents used for priming are then discarded into the waste area 120.

Thermal control in this invention is achieved using an embedded algorithm with a microprocessor based control unit to monitor and adjust the temperature of the various liquids used by this invention. The display 22 in FIG. 2 monitors temperatures of the various areas of the invention. The temperature controller 26 confirms that all the samples, factors, buffers and reagents are at the correct temperature for performing each test. In the preferred embodiment, the embedded algorithm requires:

1. an input of a temperature to voltage converter providing 16 bit conversion values.
2. an output of a programmable pulse width generator capable of driving the device of interest.
3. memory interface for setting of desired temperature, functional heating or cooling, safety limits, an integrator/differentiator value, and output thermal results.
4. a periodic interrupt generator to provide a "time domain" environment.

The algorithm uses the following variables:
1. Desired temperature: Required temp to regulate to.
2. Current temperature: Current value of the filtered temperature
3. Previous temperature: Last reading of filtered temperature.

4. Current direction: result of the current temperature minus the previous temperature
5. Error accumulator: A holding variable for results of computed errors.
6. Pulse width value: Updated value written to physical hardware.

In the "time domain environment": (processing in the interrupt event) the algorithm performs the following steps:
1. A digitized temperature input is read in, accumulated, and averaged.
2. Communication is passed for "normal processing" to compute variables.
3. The "pulse width value" variable is applied to the physical hardware.

During "normal processing time," when communication has occurred to compute variables, the "current temperature" variable is moved to the "previous temperature" variable and the "current temperature" is updated from the averaged value sent from the interrupt event. The "current direction" is computed by subtracting the "previous temperature" from the "current temperature".

The need to regulate is determined by comparing "current temperature" to the safety limits. Outside of the safety limits the algorithm removes all drive from the physical device and does no further function to determine regulation. If the temperature is within safety limits the algorithm determines whether to cool (drive to a lesser temperature) or heat (drive to a greater temperature) based on information provided by the external memory interface.

An error accumulator is added to insure that the maximum rate added (or subtracted) to the "pulse width value" provides smooth power addition (or subtraction) to the device under control The new "pulse width value" will be applied to the physical hardware the next time the "time domain environment" is entered. to built based on the following equation:

---

Value in error accumulator =
    error accumulator + ((error accumulator − ("desired
        temperature" − "current
        temperature"/gain_nibble_0) − ("current direction"
        * gain_nibble_1))/gain_nibble_2)
where gain_nibble_0, gain_nibble_1, and gain_nibble_2
represent variables contained in the integrator/differentiator
value provided by the external memory interface.
This error value is now checked for limits contained in the
integrator/differentiator value.

---

The thermal control algorithm has the benefit that it can be configured to drive either heating or cooling devices, it has built in safety devices in the event of loss of sensor input, and it uses a simplified integrator/differentiator to allow for a variety of thermal masses to be regulated.

Although the present invention has been shown and described with respect to preferred embodiments, various changes and modifications that are obvious to a person skilled in the art to which the invention pertains are deemed to lie within the spirit and scope of the invention.

What is claimed:

1. In a system for transferring a sample from a first container to a second container through an aperture in the second container, mixing the sample with at least one additional substance introduced in the second container through said aperture, and thereafter evaluating the mixed sample, the improvement comprising:
    a container handling system for confirming the proper orientation of the second container and for generating an error signal if the second container is not properly oriented.

2. The invention of claim 1 wherein the container handling system generates an error signal if the second container is not present.

3. The invention of claim 1 wherein the sample is blood and the mixed sample is evaluated for clotting time.

4. The invention of claim 1 wherein the first container is a test tube.

5. The invention of claim 1 wherein the second container is a cuvette.

6. The invention of claim 1 wherein the sample is optically evaluated.

7. The invention of claim 1 wherein the system includes a sample handler including a first rack for storage of first containers and a second rack for storage of at least one of said additional substances.

8. The invention of claim 7 wherein the sample handler further includes a bar code reader for reading bar codes on said first container.

9. The invention of claim 1 wherein the system includes a bar code reader, comprising a light source and a detector.

10. The invention of claim 1 wherein the system includes a test tube detector comprising:
    a light source; and
    means for receiving light from the light source and for indicating when the light from the light source has been at least partially interrupted.

11. The invention of claim 10 wherein the system includes a bar code reader and the light source is the light from the bar code reader.

12. The invention of claim 1 further including a fluid control system comprising:
    a needle for insertion into the first container, and
    means for detecting when a needle has reached the surface of the sample.

13. The invention of claim 12 wherein the needle and detecting means are capacitively coupled together.

14. The invention of claim 1 wherein the orientation of the second container is optically verified.

15. The invention of claim 1 wherein a plurality of second containers are positioned in a carousel, and the container handling system further includes means for releasing individual containers from the carousel.

16. The invention of claim 15 wherein the second containers are cuvettes.

17. The invention of claim 1 wherein the system further includes an optics handler comprising:
    means for dispensing at least one additional substance through the aperture into said second container.

18. The invention of claim 1 wherein the system further includes means for optically detecting the presence of said additional substance prior to transferring said additional substance to said second container.

19. The invention of claim 1 wherein the system includes at least one pump for pumping said additional substance through a delivery tube into said second container and means for self-priming said delivery tube.

20. An automated hemostasis analyzer comprising:
    a sampler handler comprising:
        test tube racks, wherein test tubes are stored, and wherein the racks can move in at least one direction;
        factor/buffer racks, wherein bottles of factor and buffers necessary for the tests are stored, wherein the racks can move in at least one direction;
    a bar code reader, comprising:
        means for detecting coded data on the test tubes;
        a test tube detector comprising:

means for light detection, wherein the light that is detected comes from the bar code reader including:
    a photodetector, for detecting light emitted from the bar code reader;
a fluid control system, comprising:
    means for determining when a needle has reached the surface of the fluid in a test tube;
    a carousel containing cuvettes;
    means for releasing cuvettes into a chute;
    cuvette verification/orientation sensors comprising:
        means for detecting whether cuvettes are aligned in the proper orientation in the chute;
        said needle for withdrawing a sample from a test tube and injecting the sample into a cuvette;
    an optics handler comprising:
        a reagent dispensing system, including:
            means for detecting presence of reagent in reagent vials;
            delivery tubes, connected to the reagent vials;
            a pumping assembly for transporting reagent to cuvettes;
    an optics assembly, further comprising:
        said pumping assembly for autopriming by filling said delivery tubes with reagents,
        means for detecting levels of reagent in said vials; and
        means for optically determining the occurrence of a reaction between the sample and reagent.

21. A method of sample handling and reaction evaluation wherein at least a portion of a sample from a first container is transferred to a second container and at least one additional substance is added to the portion of the sample to cause a reaction, comprising:
    inserting a needle into the first container; and
    detecting that said needle has reached the sample in the first container.

22. The method of claim 21 wherein the needle is capacitively coupled to a circuit and the step of detecting includes changing the output of said circuit.

23. The method of claim 21 wherein said additional substance is transferred from a storage container through a delivery tube to said second container, the method further including priming the delivery tube by filling the delivery tube with said additional substance prior to transferring said portion of the sample to the second container.

24. The method of claim 21 and further including the steps of:
    optically confirming the presence and orientation of said second container;
    optically confirming the presence of said additional substance prior to the step of transferring said additional substance to said second container; and
    optically confirming the occurrence of a reaction between the portion of the sample and the additional substance.

25. The method of claim 24 and further including the steps of:
    optically confirming the presence of the first container; and
    optically reading any data on the first container.

* * * * *

UNITED STATES PATENT AND TRADEMARK OFFICE
CERTIFICATE OF CORRECTION

PATENT NO. : 5,879,628
DATED : March 9, 1999
INVENTOR(S) : Ridgway et al.

It is certified that error appears in the above-identified patent and that said Letters Patent is hereby corrected as shown below:

On the title page item [75], change "Ridgeway" to --Ridgway--.

Signed and Sealed this

Fifteenth Day of August, 2000

Attest:

Q. TODD DICKINSON

*Attesting Officer*       *Director of Patents and Trademarks*